(12) United States Patent
Wortmann et al.

(10) Patent No.: US 7,013,705 B2
(45) Date of Patent: Mar. 21, 2006

(54) METHOD AND DEVICE FOR DETERMINATION OF THE WEAR RESISTANCE OF A SURFACE

(75) Inventors: Andreas Wortmann, Würzburg (DE); Holger Lüthje, Halstenbek (DE)

(73) Assignee: Innowep GmbH, Wurzburg (DE)

( * ) Notice: Subject to any disclaimer, the term of this patent is extended or adjusted under 35 U.S.C. 154(b) by 19 days.

(21) Appl. No.: 10/504,012

(22) PCT Filed: Feb. 7, 2003

(86) PCT No.: PCT/EP03/01243

§ 371 (c)(1),
(2), (4) Date: Aug. 6, 2004

(87) PCT Pub. No.: WO03/067222

PCT Pub. Date: Aug. 14, 2003

(65) Prior Publication Data

US 2005/0081599 A1   Apr. 21, 2005

(30) Foreign Application Priority Data

Feb. 8, 2002   (DE) ................................ 102 05 435

(51) Int. Cl.
*G01N 19/02* (2006.01)
(52) U.S. Cl. ............................................................ 73/7
(58) Field of Classification Search .................... 73/7
See application file for complete search history.

(56) References Cited

U.S. PATENT DOCUMENTS

| | | | | |
|---|---|---|---|---|
| 2,373,115 A | * | 4/1945 | Graves | 73/7 |
| 2,582,223 A | * | 1/1952 | Blackburn et al. | 73/7 |
| 2,670,627 A | * | 3/1954 | Shaw | 73/159 |
| 2,856,582 A | * | 10/1958 | Anderson | 324/554 |
| 2,929,240 A | * | 3/1960 | Williams | 73/7 |
| 3,359,783 A | * | 12/1967 | Scheiman et al. | 73/7 |
| 3,495,049 A | * | 2/1970 | Nelson et al. | 360/122 |
| 3,753,093 A | * | 8/1973 | Gardner et al. | 324/701 |
| 3,786,676 A | * | 1/1974 | Korolyshun et al. | 73/817 |
| 3,813,917 A | * | 6/1974 | Cole | 73/9 |
| 4,091,654 A | * | 5/1978 | Hurtig et al. | 73/7 |
| 4,413,513 A | * | 11/1983 | Ross et al. | 73/162 |
| 4,434,671 A | * | 3/1984 | Yamashita et al. | 73/862.473 |
| 4,459,842 A | * | 7/1984 | Kihara et al. | 73/7 |

(Continued)

FOREIGN PATENT DOCUMENTS

EP     629848 A1  *  12/1994

(Continued)

OTHER PUBLICATIONS

Van Groenou, A. Broese et al., "Quick Test on Wear of Head Materials by Recording Tapes," Int. Magn. Conf. Intermag 83 (Phila., PA., Apr. 5, 1983).

(Continued)

*Primary Examiner*—Hezron Williams
*Assistant Examiner*—John Fitzgerald
(74) *Attorney, Agent, or Firm*—Edwin D. Schindler

(57) ABSTRACT

A method and apparatus for determining the wear resistance of the surface of a sample object includes an abrasive grinding belt, run between the sample object and a counter-body, with the grinding belt being pressed against the sample object with a predetermined force by the counter-body. The position of the counter-body is determined at, at least, a first position and a second position, each occurring at two different points in time. The wear resistance of the surface of the sample object is determined from the difference in determined positions.

36 Claims, 1 Drawing Sheet

U.S. PATENT DOCUMENTS

Figure 1:
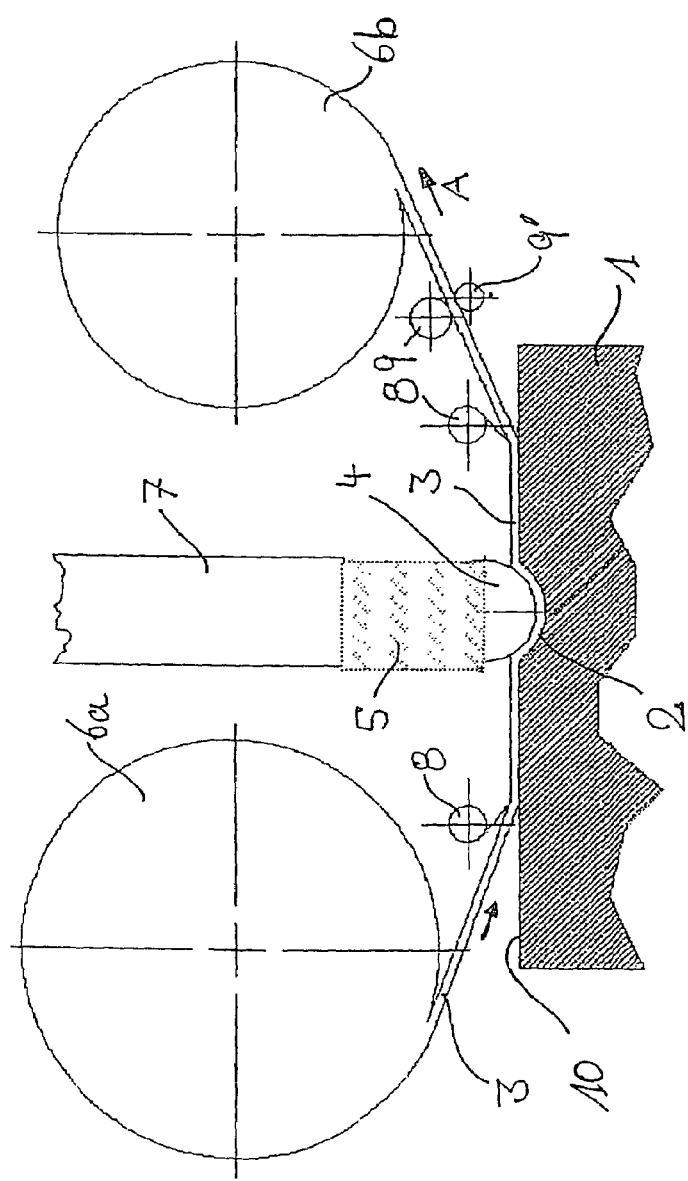

| | | | |
|---|---|---|---|
| 4,899,051 A * | 2/1990 | Helm ........................ 250/340 |
| 4,958,511 A * | 9/1990 | Marcus ............................ 73/7 |
| 5,074,983 A * | 12/1991 | Eltoukhy et al. ...... 204/192.13 |
| 5,337,608 A * | 8/1994 | Egan et al. ................. 73/865.6 |
| 5,375,451 A * | 12/1994 | Sandstrom ........................ 73/7 |
| 5,533,382 A * | 7/1996 | Clerkin ............................ 73/7 |
| 5,665,900 A * | 9/1997 | Yoo ................................ 73/7 |
| 6,131,435 A * | 10/2000 | Mishima et al. .................. 73/7 |
| 6,247,356 B1 | 6/2001 | Merck, Jr. et al. |
| 6,401,058 B1 * | 6/2002 | Akalin et al. .................. 703/7 |
| 2004/0099059 A1 * | 5/2004 | Tarumi ........................ 73/587 |

FOREIGN PATENT DOCUMENTS

| | | | |
|---|---|---|---|
| JP | 4-29035 | | 1/1992 |
| JP | 06167440 A | * | 6/1994 |

OTHER PUBLICATIONS

Van Groenou, A. Broese, "A Quick Test on Wear of Materials Used in Magnetic Recording," Conf. Wear of Materials, No. XP008017198 (Reston, VA 1983).

* cited by examiner

METHOD AND DEVICE FOR DETERMINATION OF THE WEAR RESISTANCE OF A SURFACE

BACKGROUND OF THE INVENTION

1. Field of the Invention

The present invention relates to a method for determining the wear resistance of a material surface of a sample, utilizing a counter-body and a belt, with the belt being run between the sample and a counter-body, while the belt is pressed against the sample with a previously determined force, thereby allowing for the wear resistance of the sample surface to be determined.

A related apparatus for determining the wear resistance of a material surface of a sample, comprising a counter-body and a belt is also taught, the apparatus being for holding and transport which holds and carries the belt over the sample surface. Further included is a counter-body holding device and a counter-body held by the counter-body holding device vertically movable, while the counter-body holding device is arranged so that the counter-body can be pressed on the side of the belt, which is turned away from the sample surface.

The determination of the wear resistance of very thin surface layers has quickly gained importance in industry, as considerable miniaturization efforts have progressed and innovative technologies, such as the micro-system technique, are greatly increasing. Micro tribological optimizations of rails, bearings and sliding contacts require, for example, the use of extremely thin layers, which thicknesses are very often on the sub-micro scale and which have to be tested and optimised optimized regarding their mechanical wear resistance. The prior art fails to disclose adequate methods and devices for accomplishing these tasks.

2. Description of the Prior Art

The known micro-scratch tester based on the AFM method is not suitable for the determination of practically usable and transferable results since the scratch results, which are gained with the aid of a thin needle, permit no determination regarding the actual areal wear in practice.

For a local resolution examination of wear characteristics on material surfaces, the ball wear method is used. Here, calotte shaped grindings are produced by a 3-body-contact on the surface, which is to be measured. Optically measured, the grindings allow conclusions about wear resistance. The grinding is produced by a ball turning on the material surface, which is moistened with a polishing slurry.

It is disadvantageous that the polishing medium can cause a change its grinding characteristics, for example, by being soiled with abraded material, by deposit of particles and by evaporation losses of the fluid. The polishing slurry can, furthermore, operate as a wear passive material when particles deposit in soft surfaces and it is unevenly spread over the counter-body's contact route. The surface of the ball is also altered. A frequently change of balls is necessary.

Furthermore, this prior art method of load variation is limited by a reduction of the calotte radius. Also, the pressure force of the ball can only be used restrictively. When evaluating the measurement, failures of the calotte form (especially rounding of the edges) can falsify the measurement results.

In summation, all of the prior art testing methods provide only limitedly transferable results for each application (scratch-test) or cannot be restricted to small lateral areas to be analyzed (sand trickle test).

Using the reflection method for testing lacquers, the results show great dispersion, while the Taber test does not allow an analysis of extremely thin surface areas.

A further testing device for determining the abrasive wear resistance of magnetic heads in video recorders is published in Bushan, B. et al. "Tribology and Mechanics" Sp. 22, ASLE Spec. Publ. Park Ridge 1987 from van Groenou et al. In this so-called "Sphere-on-Tape-Test," a tape with an abrasive effect is run between a sample surface and a lateral fixed, weight loaded counter-body ball. The abrasive tape is pressed on the sample by the pressure of the counter-body ball, so that a wear calotte is formed on the sample surface. The sample is then taken out of the device at different points of time and the depth of the calotte is measured.

With this device, for example, deviations of the tape thickness or complicated topographies of the samples lead to damping difficulties. Furthermore, no exact sample positioning control is possible and, due to the removal and fixing of the sample in the device, an automation of the measurement is not feasible. Consequently, an in situ wear measurement is not possible.

From the conference contribution (international conference on wear of materials in 1983) of Broese van Groenou, among others, wear magnet recorders were examined. For these devices, a running through belt is pressed with its coating, which is equipped with magnet porter information, against a sample with the assistance of a counter-body. For determining the wear, the generated deepening in the sample body is measured after removing the belt and the wear is determined. In a disadvantageous way, a method of this kind does not allow an in situ measurement. As the wear is generated by the magnetic coating, the material of the belt itself remains without influence.

Finally, U.S. Pat. No. 6,247,356 B1 shows a device for testing the hardness of materials.

SUMMARY OF THE INVENTION

An object of the present invention is to provide a method and related apparatus for determining the mechanical wear resistance of a sample surface, which can also be used for reliably determining the wear resistance of extremely thin surface installations and coatings, at favorable costs and quickly.

The object of the invention is fulfilled by the claimed method and the apparatus, wherein the wear resistance of the surface of a sample object includes an abrasive grinding belt which is run between the sample object and a counter-body, with the grinding belt being pressed against the sample object with a predetermined force by the counter-body. The position of the counter-body is determined at, at least, a first position and a second position, each occurring at two different points in time. The wear resistance of the surface of the sample object is determined from the difference in determined positions.

According to the present invention the claimed method differs from the prior art by determining the position of the counter-body at, at least, two different points of time. The advantage is that the position of the counter-body, in situ, during the wear test is measured. The depth of the wear calotte in the sample's body can be determined from the position of the counter-body.

The increase of the depth is correlated to the wear resistance of the sample surface. In this manner, a simplified measurement and interpretation of the wear measurement is possible.

The sample objects can be constructed small and mobile, although a measurement is possible on both large and small objects.

Measurements of surface areas up to a dimension of 10 nm or localized measurements on surfaces down to 10 micro-m$^2$ are possible. Wear resistance on the edges of a sample are feasible with the claimed method. By an appropriate controlled load on the counter-body, standardized work parameters, as well as an elimination of the influence of thickness variations of the wear belt, are practicable.

The method according to the invention can be utilized manifoldly. It can be used, for instance during quality control and in the field of research and development, for example, for lacquer coatings, for the sealing of floors, for the quality control of micro-edifice elements (MEMS) or in the micro-system technique. Particularly, a fast assessment of wear hard-material-layers in the field of coating techniques (galvanizing, varnishing, material coating procedures in general) is possible. The method of the present invention also can be used as optimization tool during the layer process development (e.g. in the field of galvanic, CVD, PVD).

DETAILED DESCRIPTION OF THE PREFERRED EMBODIMENTS

Since the determination of the position of the counter-body can be made, in situ, the tape thickness variation can be eliminated from the measurement by running back the belt into the same position at the respective measurement points of time. So the position of the counter-body is always able to be determined with the same tape thickness. The measurement of the counter-body's position can be made when the tape is stopped at one patch of the tape, which has not been used for generating wear. This has a particular importance, when calotte-depths are measured in a range of 10 nm, while the tape thickness is usually >10 micrometers (typically 10–20 micrometers) and up to a thousand times of the produced calotte-depth. This also enables the resolution of calotte-depths of a scale of 1 nm. Customary magnet tapes can be used as tapes, which enable the marking and of a certain tape position, so that the belt can be run back into the marked position for the single measurement points of time without pressure or load and, if applicable, without further contact with the counter-body body and/or the sample surface. Of course, a position, which is relatively staggered to the measurement position of the tape, can be marked. The utilized grinding belts are in this case advantageously conventional audio or videotapes with a RMS roughness of 10 to 30 nm. In the case of magnetic tapes, the marking of the tape position used for the measurement can be made and/or recorded magnetically. As a holding and transport device for these belts, customary tape transporting units, such as, VCR and MC drives can be used, for example, from mobile devices.

The measurement of the counter-body's position can be made capacitative, inductive or interferometric. In the latter case, the counter-body itself can be equipped with a reflector. The force on the counter-body for pressing the tape against the sample surface can be produced capacitatively (AFM), magnetically or even inductively (touch method). The adjustment of the force can be accomplished with significant flexibility using the inventive method, so that the damping behavior is controllable, and even with higher belt speeds micro-calottes, with an extraordinarily good surface smoothness and without grind grooves being produced. For a magnetic generation of force, permanent and/or electro magnets are suitable.

The counter-body can be a ball or a cylinder. When using a rolling ball or a rolling cylinder the damage on the back of the tape is reduced by the abrasion of the ball and the grinding belt. Further, the abrasion of the ball is also reduced. The counter-body can also be tribologically optimally coated for reducing the friction and the abrasion between the counter-body and the grinding belt.

Further, advantageous coatings refer to the adjustment of the nano/micro topography of the grinding belt surface, which comes in contact with the sample surface, for example, though plasma or ion corrosion. The grinding belt can also be adhesively coated on the abrasive side, e.g., by CVD or PVD methods, for example, steaming or sputtering, for being able to record an adhesive abrasion as well.

For evaluating the measurement, a depth criterion can be used for example. In this case, the abrasive belt runs until a certain depth criterion for the produced calotte in the sample surface is achieved. The depth criterion can be controlled by measuring the position of the counter-body after certain time distances or continuously. If the depth criterion is reached, the required space of time or the length of the belt, which was producing this calotte run-ning through between the counter-body and the sample, can be determined. The period of time or the belt length now correlate with the wear resistance of the surface sample.

In the following, an example of an apparatus and a method according to the invention is described.

BRIEF DESCRIPTION OF THE DRAWING FIGURE

The single FIGURE provides an elevational view of one preferred embodiment of the apparatus and method of the present invention.

DETAILED DESCRIPTION OF THE DRAWING FIGURE

FIG. 1 shows a device for measuring the wear resistance of a sample body 1. The sample body 1 has a surface 10, on which a counter-body, formed as hemisphere 4, is pressed. Between the counter-body 4 and the surface 10 of the sample body 1, an abrasive belt 3 is run through. Belt 3 is unwinded from a spool 6a and wind up onto spool 6b, while being transported by transport rolls 9, 9' and run parallel to the surface 10 of the sample body 1, with the assistance of suppressing pressing devices 8. A roll rail 6a, 8, 9, 9' is of the kind generally found, for example, in a conventional portable audio or videotape apparatus.

The hemisphere 4 is now fixed by a holding device 5, referring to movements in the plane surface 10, although holding device 5 makes vertical movements of the hemisphere 4 to the surface 10 possible. The hemisphere 4 is furthermore connected to a unit 7, which puts a load on the hemisphere 4, and contains a measurement unit for determining the vertical position of hemisphere 4.

By virtue of unit 7, the hemisphere 4 is now pressed with a defined force on the magnet belt 3, so that it is forced into frictional contact with the surface 10 of the sample body 1 and produces a wear, or abrasion, calotte 2 during the run of the belt. In FIG. 1, the depth of the wear calotte 2 is illustrated in an exaggerated fashion as compared to the thickness of the tape 3, since the thickness of the tape is usually about a thousand times larger than the depth of the produced calotte (with a depth of down to 1 nm).

The measuring unit 7 contains here, for example, an interferometer, which sends a ray of light on the plane surface of the hemisphere 4, which is turned away from the grinding belt. The ray of light is reflected from that surface and measured in the interferometer 7. From this measurement, the position of the hemisphere 4 and, with timely distanced measurements, the depth, as well as the change of depth, of the calotte 2 can be determined.

The invention claimed is:

1. A method for determining wear resistance of a material surface object sample, comprising the steps of:
   running an abrasive grinding belt between a sample object and a movable counter-body;
   pressing said abrasive grinding belt with said movable counter-body by applying a predetermined force against said sample object;
   determining at least a first position and a second position of said movable counter-body at, at least, a first point in time and a second point in time, respectively, while said running said abrasive grinding belt between said sample object and said movable counter-body;
   calculating wear resistance of said sample object by measuring a difference in distance between, at least, said first position and said second position of said movable counter-body.

2. The method for determining wear resistance of a material surface object sample according to claim 1, wherein said step of at least said first position and said second position of said movable counter-body is carried out by running backward said abrasive grinding belt, so that said first position is the same as said second position.

3. The method for determining wear resistance of a material surface object sample according to claim 1, wherein said step of at least said first position and said second position of said movable counter-body is carried out by magnetic markings.

4. The method for determining wear resistance of a material surface object sample according to claim 1, wherein said step of at least said first position and said second position of said movable counter-body is carried out on a continuous basis.

5. The method for determining wear resistance of a material surface object sample according to claim 1, wherein said step of pressing said abrasive grinding belt with said movable counter-body by applying a predetermined force against said sample object is carried out by moving said counter-body vertically relative to a surface of said abrasive grinding belt.

6. The method for determining wear resistance of a material surface object sample according to claim 1, wherein said step of pressing said abrasive grinding belt with said movable counter-body by applying a predetermined force against said sample object is carried out by fixing said first position of said movable counter-body and moving said abrasive grinding belt within the plane of a surface of said abrasive grinding belt.

7. The method for determining wear resistance of a material surface object sample according to claim 1, wherein said step of determining at least a first position and a second position of said movable counter-body is performed capacitatively.

8. The method for determining wear resistance of a material surface object sample according to claim 1, wherein said step of determining at least a first position and a second position of said movable counter-body is performed inductively.

9. The method for determining wear resistance of a material surface object sample according to claim 1, wherein said step of determining at least a first position and a second position of said movable counter-body is performed optical interometrically.

10. The method for determining wear resistance of a material surface object sample according to claim 1, wherein said movable counter-body is a ball.

11. The method for determining wear resistance of a material surface object sample according to claim 1, wherein said movable counter-body is a cylinder.

12. The method for determining wear resistance of a material surface object sample according to claim 1, wherein said step of pressing said abrasive grinding belt with said movable counter-body is carried out by using a mass of said abrasive grinding belt.

13. The method for determining wear resistance of a material surface object sample according to claim 1, wherein said step of pressing said abrasive grinding belt with said movable counter-body is carried out by using means for applying a predetermined force for pressing said abrasive grinding belt.

14. The method for determining wear resistance of a material surface object sample according to claim 13, wherein said means for applying a predetermined force for pressing said abrasive grinding belt is a mechanical compensation system.

15. The method for determining wear resistance of a material surface object sample according to claim 13, wherein said means for applying a predetermined force for pressing said abrasive grinding belt is an inductive force generating system.

16. The method for determining wear resistance of a material surface object sample according to claim 13, wherein said means for applying a predetermined force for pressing said abrasive grinding belt is a magnetic force generating system.

17. The method for determining wear resistance of a material surface object sample according to claim 13, wherein said means for applying a predetermined force for pressing said abrasive grinding belt is a capacitative force generating system.

18. An apparatus for determining wear resistance of a material surface object sample, comprising:
   an abrasive grinding belt;
   means for retaining and transporting said abrasive grinding belt over a material surface object sample;
   a counter-body;
   means for retaining and moving said counter-body;
   means for pressing said counter-body upon a surface of said abrasive grinding belt with said abrasive grinding belt running between the material surface object sample and said counter-body; and,
   means for measuring a position of said counter-body from a first position to a second position.

19. The apparatus for determine determining wear resistance of a material surface object sample according to claim 18, wherein said means for measuring a position of said counter-body measures said first position and said second position at, at least, two different points in time.

20. The apparatus for determining wear resistance of a material surface object sample according to claim 18, wherein said means for measuring a position of said counter-body measures said first position and said second position on a continuous basis.

21. The apparatus for determine determining wear resistance of a material surface object sample according to claim 18, further comprising means for marking said first position and said second position of said counter-body and means for subsequently recognizing said marking of said first position and said second position of said counter-body.

22. The apparatus for determine determining wear resistance of a material surface object sample according to claim 18, wherein said means for retaining and moving said counter-body vertically moves said counter-body relative to the surface of said abrasive grinding belt.

23. The apparatus for determining wear resistance of a material surface object sample according to claim 18, wherein said means for retaining and moving said counter-body fixes movement of said counter-body relative to the surface of said abrasive grinding belt.

24. The apparatus for determining wear resistance of a material surface object sample according to claim 18, wherein said means for measuring a position of said counter-body is a capacitative measuring device.

25. The apparatus for determining wear resistance of a material surface object sample according to claim 18, wherein said means for measuring a position of said counter-body is an inductive measuring device.

26. The apparatus for determining wear resistance of a material surface object sample according to claim 18, wherein said means for measuring a position of said counter-body is an optically interometrical measuring device.

27. The apparatus for determining wear resistance of a material surface object sample according to claim 18, wherein said counter-body is a cylinder.

28. The apparatus for determining wear resistance of a material surface object sample according to claim 18, wherein said counter-body is a ball.

29. The apparatus for determining wear resistance of a material surface object sample according to claim 18, further comprising means for steering and moving said abrasive grinding belt to a predetermined belt position for determining a position of said counter-body.

30. The apparatus for determining wear resistance of a material surface object sample according to claim 18, further comprising:
    means for marking said abrasive grinding belt at a predetermined belt position; and,
    means for recognizing said marking of said abrasive grinding belt at said predetermined belt position.

31. The apparatus for determining wear resistance of a material surface object sample according to claim 18, wherein said counter-body is coated.

32. The apparatus for determining wear resistance of a material surface object sample according to claim 18, wherein said means for pressing said counter-body upon the surface of said abrasive grinding belt is a force-generating system.

33. The apparatus for determining wear resistance of a material surface object sample according to claim 32, wherein said force-generating system is a mechanical compensation device.

34. The apparatus for determining wear resistance of a material surface object sample according to claim 32, wherein said force-generating system is an inductive force-generating system.

35. The apparatus for determining wear resistance of a material surface object sample according to claim 32, wherein said force-generating system is a magnetic force-generating system.

36. The apparatus for determining wear resistance of a material surface object sample according to claim 32, wherein said force-generating system is a capacitative force-generating system.

* * * * *